(12) United States Patent
Nelms et al.

(10) Patent No.: US 8,081,813 B2
(45) Date of Patent: Dec. 20, 2011

(54) SYSTEM FOR ASSESSING RADIATION TREATMENT PLAN SEGMENTATIONS

(75) Inventors: Benjamin E. Nelms, Merrimac, WI (US); Neal R. Miller, Middleton, WI (US); Jeffrey H. Manion, Waunakee, WI (US)

(73) Assignee: Standard Imaging, Inc., Middleton, WI (US)

( * ) Notice: Subject to any disclaimer, the term of this patent is extended or adjusted under 35 U.S.C. 154(b) by 398 days.

(21) Appl. No.: 12/475,139

(22) Filed: May 29, 2009

(65) Prior Publication Data

US 2009/0297014 A1    Dec. 3, 2009

Related U.S. Application Data

(60) Provisional application No. 61/057,554, filed on May 30, 2008.

(51) Int. Cl.
*G06K 9/00* (2006.01)
*A61N 5/10* (2006.01)

(52) U.S. Cl. .................... 382/132; 382/128; 378/65

(58) Field of Classification Search .......... 382/128–132, 382/173, 199; 378/65, 62; 600/425; 250/252.1
See application file for complete search history.

(56) References Cited

U.S. PATENT DOCUMENTS

| | | | | |
|---|---|---|---|---|
| 6,728,334 | B1 * | 4/2004 | Zhao | 378/62 |
| 7,200,251 | B2 * | 4/2007 | Joshi et al. | 382/128 |
| 7,343,030 | B2 * | 3/2008 | Sawyer | 382/128 |
| 7,367,955 | B2 * | 5/2008 | Zhang et al. | 600/534 |
| 7,606,405 | B2 * | 10/2009 | Sawyer et al. | 382/128 |
| 7,889,906 | B2 * | 2/2011 | Smith et al. | 382/132 |
| 7,945,022 | B2 * | 5/2011 | Nelms et al. | 378/65 |
| 2003/0138077 | A1 * | 7/2003 | Lee | 378/65 |
| 2005/0077459 | A1 * | 4/2005 | Engler et al. | 250/252.1 |
| 2005/0207630 | A1 * | 9/2005 | Chan et al. | 382/131 |
| 2009/0292200 | A1 * | 11/2009 | Kindlein et al. | 600/425 |
| 2009/0324078 | A1 * | 12/2009 | Wu et al. | 382/173 |

OTHER PUBLICATIONS

Wijesooriya, Krishni, et al., Med. Phys. 35 (4) pp. 1251-1260, Apr. 2008, American Association of Physicists in Medicine, College Park, Maryland, USA.

\* cited by examiner

*Primary Examiner* — Sang Nguyen
(74) *Attorney, Agent, or Firm* — Boyle Fredrickson, S.C.

(57) ABSTRACT

Segmentations used to describe structures to be treated by radiotherapy are evaluated by converting the segmentations into volume models and examining volume elements that are extra or missing in the volume model of the second segmentation with respect to the volume model of the first segmentation. This characterization of volume elements may be displayed graphically to show differences in segmentations for training or evaluation purposes and may be quantified by a metric method tallying volume elements as optionally weighted by distance from volume elements shared by the segmentation.

18 Claims, 5 Drawing Sheets

SYSTEM FOR ASSESSING RADIATION TREATMENT PLAN SEGMENTATIONS

CROSS-REFERENCED TO RELATED APPLICATION

This application claims the benefit of U.S. provisional application 61/057,554 filed May 30, 2008 and hereby incorporated by reference.

BACKGROUND OF THE INVENTION

Medical equipment for radiation therapy treats tumorous tissue with high-energy radiation. The amount of radiation and its placement must be accurately controlled to ensure both that the tumor receives sufficient radiation to be destroyed, and that the damage to the surrounding and adjacent non-tumorous tissue is minimized.

In external source radiation therapy, a radiation source external to the patient treats internal tumors. The external source is normally collimated to direct a beam only to the tumorous site. The source of high-energy radiation may be from linear accelerators as x-rays, or electrons, protons, neutrons or any other form, in the range of 2-300 MeV, or gamma rays from highly focused radioisotopes such as a Co60 source having an energy of 1.25 MeV.

Typically, the tumor will be treated from several different angles with the intensity and shape of the beam adjusted appropriately. The purpose of using multiple beams, which converge on the site of the tumor, is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form a treatment plan for that tumor.

More-advanced, highly accurate modalities of radiation delivery have been developed to further customize a treatment plan to conform dose to a target region while limiting dose outside that target. Such modalities modulate individual "beamlets" of radiation within each beam so that all beamlet from all beams, in sum, create an optimal plan. Beamlet modulation may be achieved in many ways, including: temporal motion of multi-leaf collimators during delivery, rotational beams with moving collimators, solid physical modulator that optimizes the beam through a precision milled device, and non-coplanar robotic arms delivering many small, distinct beams from many angles.

In order to take advantage of the improved accuracy in dose placement offered by such optimized radiation planning and delivery systems, the radiation treatment plan may be based on a digitized virtual model of the patient's anatomy, which is built using volumetric medical imaging. The most common in volumetric medical imaging modalities are computed tomography ("CT") and magnetic resonance imaging ("MRI") As is known in the art, a CT image is produced by a mathematical reconstruction of many projection images obtained at different angles about the patient to provide an image of "slices" or planes throughout the patient.

Using the stack of CT images, the radiologist views the tumorous area and determines the beam angles and intensities (identified with respect to the tumor image) which will be used to treat the tumor. Different regions may be defined within each slice plane of a series of CT images in a process known as "segmentation." For example, regions to receive high-dose may be defined on each CT image by creating segmentation of "target areas" in that image, whereas regions that should be spared radiation because of radiation sensitivity may also be segmented in that 2D image to help guide the treatment planner on where to avoid high doses. Additional areas of segmentation may also be defined with different dose levels. This process is repeated for multiples adjacent CT images to provide a three-dimensional segmentation.

The segmentation may be done manually by clinicians (i.e. a trained dosimetrist may segment the critical sparing organs, while a physician may define the target regions) or by using various automatic segmentation programs such as those commercially available from Varian Medical Systems, Inc. of California, USA under the Eclipse "Smart Segmentation" trade name, from Royal Philips Electronics of the Netherlands in their Pinnacle system under the trade designation "Model-based Segmentation," and from CMS, Inc of Missouri, USA under the trade name "Atlas-based Autosegmentation." The results of the segmentation are stored in segmentation files, currently under a DICOM standard as DICOM-RT Structure Set files. These files contain point data defining the periphery of a volume in multiple parallel planes or slices.

SUMMARY OF THE INVENTION

The present invention provides a system for assessing segmentations from various sources. For example, a "gold standard" segmentation approved by a clinician (a physician or senior dosimetrist) may be compared against segmentation provided by clinicians in training or different software systems, and/or the segmentation from different software systems may be compared against each other.

In a preferred embodiment, the comparison process accepts as inputs, segmentations, or "regions of interest" (ROIs) recorded in electronic files, for example, using the DICOM-RT standard. The segmentations are converted to volume models and the volume models are compared to identify volume elements that are missing or extra between the first and second segmentation. The missing and extra volume elements may be measured and optionally weighted according to their distance from the reference (i.e. "correct") volume elements to produce an output indicating the quality of the one segmentation with respect to the other.

The invention may also be used for periodic quality assurance of autosegmentation routines or evaluation of those routines when they are updated or used with new imaging technology.

Specifically, then the present invention provides an apparatus for automatically assessing radiation therapy segmentations. The apparatus uses an electronic computer executing a stored program to receive a first and second electronic file each providing data points describing different three-dimensional surfaces circumscribing a structure in a human patient intended for radiation therapy. The files are used to generate a first and second volume model, per ROI, defined by the first and second electronic file respectively. These volume models are compared to identify common volume elements in common to both of the first and second volume models, missing volume elements of the first volume model that are not in the second volume model, and extra volume elements of the second volume model that are not in the first volume model. A measure of a conformance between the three-dimensional surfaces circumscribing the structure defined by the first and second electronic files is then output based on a metric method measuring numbers of missing volume elements and extra volume elements.

It is therefore one feature of at least one embodiment of the invention to provide a tool for comparing the quality of segmentations from different sources and, thus, that is generally useful for training, evaluation and product evaluation purposes.

The first and second volume models may be constructed by identifying a set of voxels within the three-dimensional surfaces, and the step of comparing the first and second volume models may evaluate each voxel of a union of the set of voxels of the three-dimensional surfaces on a voxel by voxel basis to identify and measure the missing and extra volume elements.

It is therefore one feature of at least one embodiment of the invention to provide a simple method of comparing segmentation volumes through the use of digitized volume elements readily processed by digital computer hardware.

The electronic computer may include a graphic display screen and the stored program may display a cross-sectional image through the first and second volume models along a user-defined cross-sectional plane separately identifying the common volume elements, missing volume elements, and extra volume elements by different colors.

It is therefore one feature of at least one embodiment of the invention to provide an output that can assist a user in improving their segmentation skills or autosegmentation programs by identifying not simply quality of the segmentation but the regions of error.

The common volume element elements may be colored green, the missing volume element elements blue and the extra volume element elements red.

It is therefore one feature of at least one embodiment of the invention to provide an intuitive display form that can be rapidly assessed by an individual with minimal training.

The stored program may further receive a third electronic file providing a cross-sectional image of patient tissue at the user defined cross-sectional plane, and the cross-sectional images through the first and second volume models may be displayed superimposed on the cross-sectional image of patient tissue obtained from a third electronic file.

It is therefore one feature of at least one embodiment of the invention to permit the review of segmentation region differences against the underlying data used for the segmentation, providing additional instructive detail for an individual improving his or her skills or for an individual assessing an autosegmentation program.

The metric method may provide a summation of a first function based on the missing volume elements and a second function based on the extra volume elements so that the metric method increases monotonically with increased missing volume elements and extra volume elements.

It is therefore one feature of at least one embodiment of the invention to provide a system that is sensitive both to overinclusive segmentation and underinclusive segmentation, both of which can have significant clinical effects.

The step of comparing the first and second volume models may also identify a distance measure for each missing volume element from a closest common volume element and a distance measure for each extra volume element from a closest common volume element wherein the distance measure provides a variable for weighting of the volume of each missing volume element and each extra volume element in the metric method.

It is therefore one feature of at least one embodiment of the invention to discount the influence of errors close to the desired segmentation surface but to emphasize errors far from the segmentation surface to approximate the clinical significance of these elements given the limits of resolution of typical radiation therapy systems.

The electronic computer may include a user input device for accepting a representation of the metric method to allow a user to set the metric method.

It is therefore one feature of at least one embodiment of the invention to permit wholly customized metric methods as knowledge in this area in advances.

The metric method may be a combination of: a constant value, a linear function of a number of error volume elements with distance, and an exponential function of the number of error volume elements with distance; wherein the error volume elements are missing volume elements and/or extra volume elements.

It is therefore one feature of at least one embodiment of the invention to provide a simple method of constructing complex functional metric functions by specifying simple parameters associated with constant, linear, and exponential functions.

The electronic computer may display a histogram showing cumulative missing volume elements as a fiuction of distance ranges and cumulative extra volume elements as the function of distance ranges.

It is therefore one feature of at least one embodiment of the invention to provide a display that reveals possible systematic distance errors and different distance related error trends.

The first and second electronic files may provide text strings identifying the structure and the stored program may select the metric method from a set of metric methods according to a table mapping the text strings identifying the structure of the first and second electronic files to one of the set of metric methods to be used as the metric method.

It is therefore one feature of at least one embodiment of the invention for different metric methods to be applied to different structures automatically or semi-automatically based on common structure descriptors.

The stored program may further execute to display a function of the metric method as a graph together with function parameters entered by the user and to change the graph as the function parameters are changed by the user.

It is therefore one feature of at least one embodiment of the invention to provide a graphic representation of the metric method to assist in development of custom metric methods.

These particular features and advantages may apply to only some embodiments falling within the claims and thus do not define the scope of the invention.

DETAILED DESCRIPTION OF THE PREFERRED EMBODIMENT

Figure 1:
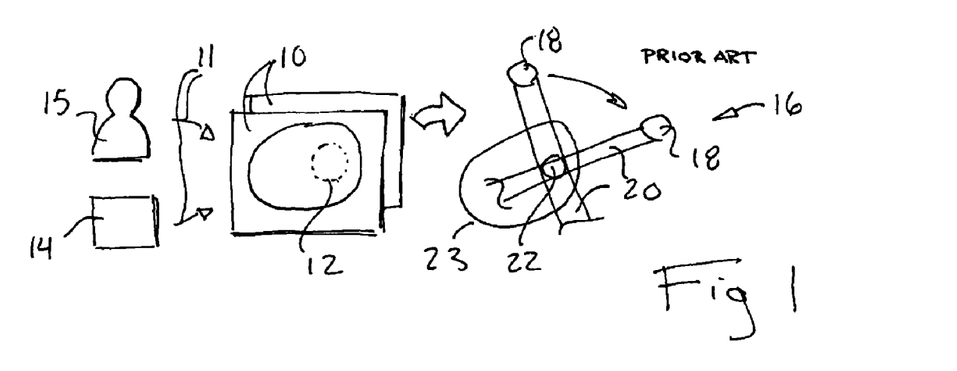
FIG. 1 is a simplified representation of the electronic files used to record segmentations for patient structures and their use in radiation therapy.

Referring now to FIG. 1, a set of electronic segmentation files 10 may be prepared as indicated using a segmentation process 11 by either a clinician 15 or through the use of an autosegmentation program 14 as is understood in the art and described generally above in the Background Of The Invention. The segmentation files 10 typically provide image-like data depicting a segmentation 12 in the form of a set of points on one or more image planes defining a periphery of a structure 22 within the patient 23.

The preparation of the segmentation files 10 is normally conducted by viewing a set of sequential slice images (not shown) obtained by a conventional medical imaging device such as a CT or MRI scanner. In the case where the segmentation files 10 are prepared by the clinician 15, the points of the segmentation 12 may be traced on the slice images. In the case where the segmentation files 10 are prepared by an autosegmentation program 14, the program analyzes variations in the data of the images against a knowledge of anatomy with general guidance by a clinician 15.

As is understood in the art, the segmentation files 10 may be used to guide a radiation therapy machine 16 having a fixed, movable radiation and/or rotational source 18 that may project a radiation beam 20 at a variety of angles about a patient 23 toward an internal structure 22. The alignment and intensity of the radiation beams 20 are guided by the segmentation files 10 and dose values associated therewith. Typically, a segmentation file 10 will include information identifying the patient and naming the structure 22, information describing the units and orientation of the segmentation 12, and may include other information for operating the radiation therapy machine 16.

Figures 2, 3:
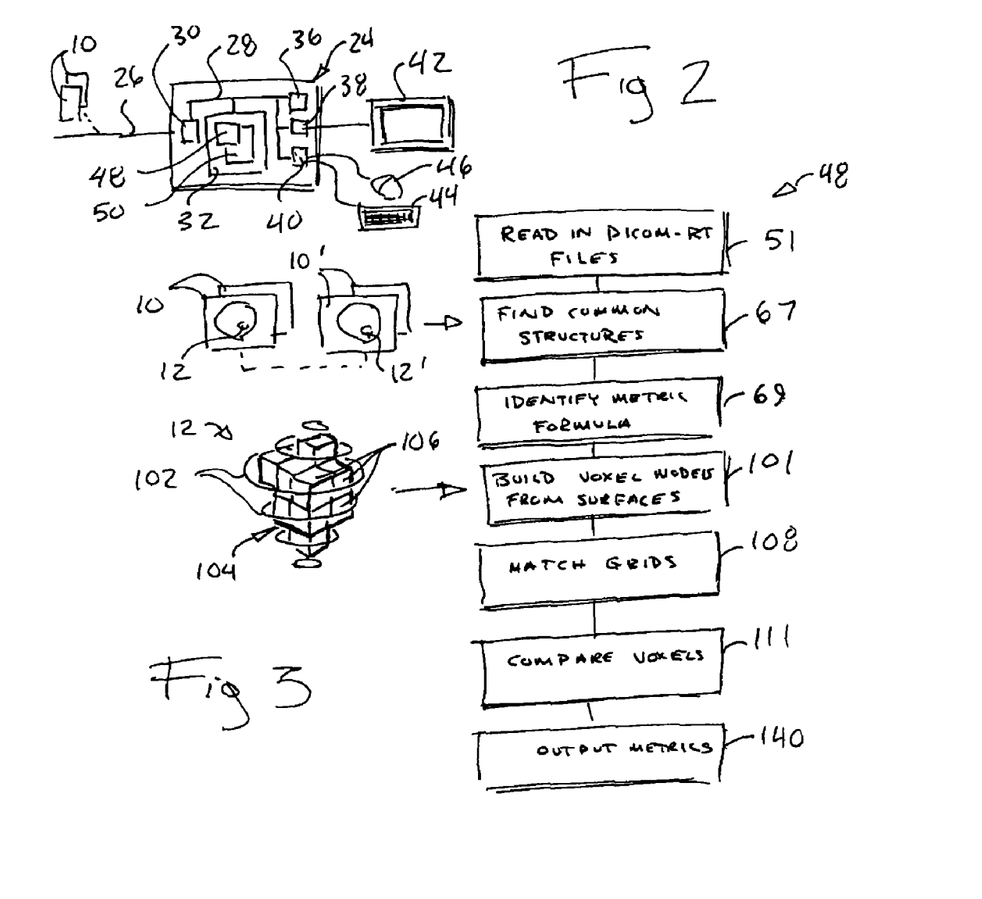
FIG. 2 is a block diagram of a computer suitable for practice of the present invention.
FIG. 3 is a flow chart showing processing of the files of FIG. 1 with respect to the present invention.

Referring now to FIGS. 1 and 2, the present invention may provide a program executable on a standard electronic computer 24 that may receive a different segmentation file 10 related to identical structure 22 in order to evaluate the quality of the segmentations of the segmentation files 10 or to evaluate the segmentation process. The electronic computer 24 may receive the segmentation files 10, for example, over a network connection 26 from a file server or by means of any suitable storage media such as optical discs, flash drives, and the like, through a media reader (not shown) and would have the ability to provide a printed output through a printer (not shown).

The electronic computer 24 may provide an internal bus 28 connecting: a network interface 30 communicating with the network connection 26, a memory 32, a processor 36, a graphics interface 38, and a user input interface 40, all of types known in the art. The graphics interface 38 may connect to a graphics display screen 42 allowing the computer 24 display images and text. The user input interface 40 may connect to a keyboard 44 or cursor control device 46 or the like or any other device allowing input by the user. The processor 36 executes a stored program 48 of the present invention using an operating system 50.

Referring now to FIG. 3, the stored program 48 of the present invention provides, at a first step indicated by process block 51, an inputting of two or more electronic segmentation files 10 providing for segmentations 12 for the same structure 22 (as shown in FIG. 1) but from a different source. For example, the first electronic segmentation file 10 may be one prepared by an experienced clinician to provide a "gold standard" segmentation for the structure 22. The second segmentation file 10' may be a segmentation by a less experienced clinician who is being trained or by an autosegmentation program being evaluated.

Figure 4:
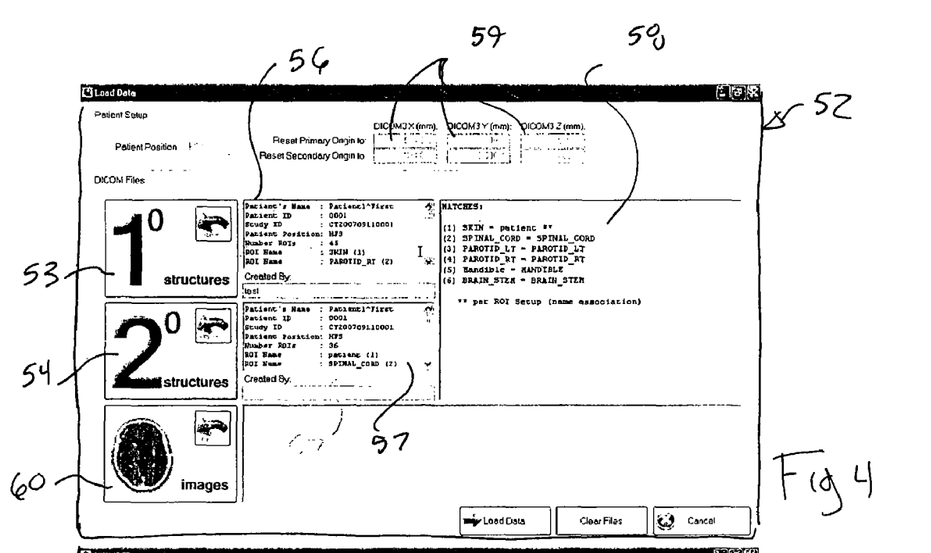
FIG. 4 is a first interface screen produced by the present invention and used for identifying electronic files for the evaluation process of the present invention.

Referring now also to FIG. 4, the program 48 may produce a first interface screen 52 on the graphics display screen 42 allowing identification and loading of the segmentation files 10 per process block 51 of FIG. 3. A first segmentation file 10 may be identified by clicking on a display button 53 to invoke a standard file browser window (not shown) allowing identification of a particular segmentation file 10 that will be used as a "standard" file in the comparison process and denoted as file 1. A data box 56 in the same row as the button 53 provides information about the segmentation file 10 identified in this process as extracted from the segmentation file 10 to assist in its proper verification. Similarly, a second button 54 may be pressed to identify a second segmentation file 10' that will be used as the "compared" file and denoted as file 2. Again the second column in this row provides a data box 56 providing details about the segmentation files 10' to assist in its identification.

A third column in common with the first and second rows holding buttons 53 and 54 provides a text box 58 identifying structures 22 of the first and second segmentation files 10, 10' by text strings embedded in the segmentation files 10, 10' and showing those structures 22 (for example, "SPINAL CORD") that are in common between the first and second segmentation files 10, 10'. Only segmentations 12 for structures 22 matching in these two segmentation files 10, 10' will be compared. The identification of common structures may be by means of the structure names embedded in the segmentation files 10, 10' and matched using well known string matching algorithms per process block 67 of FIG. 3.

A third button 60 operates in a manner analogous to that described above with respect to buttons 53 and 54 to load an image file providing a medical image of the structures 22 being segmented in the segmentation files 10, 10' that is typically the same image(s) used for the segmentation process 11. Any spatial offset among the segmentations 12 of the first and second segmentation files 10, 10' can be corrected by origin reset entry boxes 59 to ensure that the segmentations 12 are all aligned with the common origin.

Figure 5:
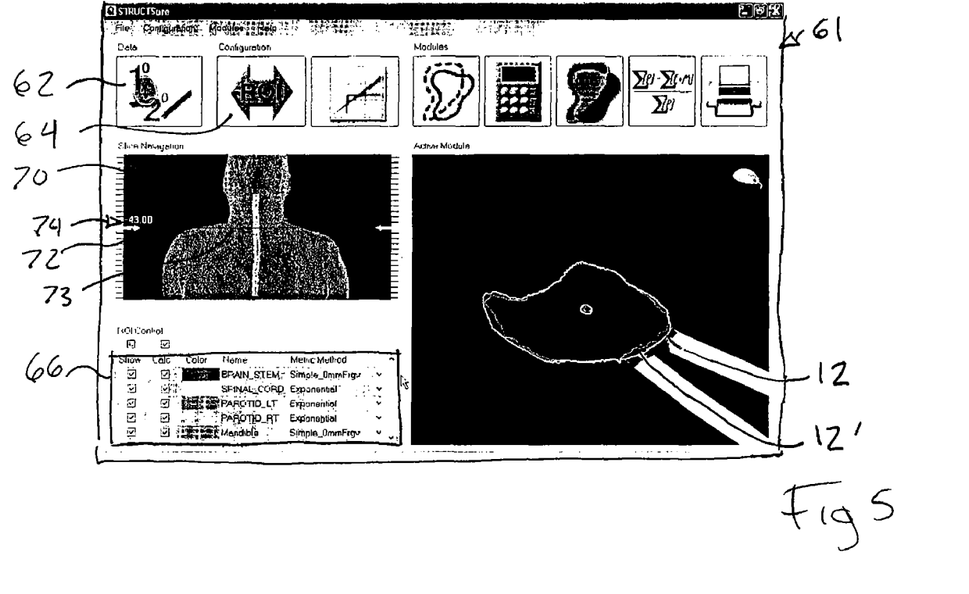
FIG. 5 is figure similar to that of FIG. 4 showing a display of segmentations for two files for a given structure at a cross-sectional plane selected by the user.

Referring now to FIG. 5, the previous interface screen 52 may be invoked by a menu button 62 visible at a start up screen (not shown) and for most subsequent screens.

Referring still to FIG. 5, pressing a second menu button 64 provides a new interface screen 61 allowing particular matching structures displayed in text box 58 to be selected per selection box 66 using checkboxes. The outlines defining the segmentations 12 of the segmentation files 10, 10' for the selected structures 22 are then displayed in spatial alignment on cross-sectional display 68 in an outline color selected at the selection box 66 (specified in the structure RT file).

In the cross-sectional display 68, the cross-sectional plane of the display is selected by the user using a plane identification window 70 showing an elevational view of the patient 23 and a cut line 73 being an edgewise view of the cross-sectional plane and by "dragging" arrow 72 up or down using the cursor control device 46 of FIG. 2 or by changing a slice number 74 on a display. At the selected cross-sectional plane, the corresponding segmentation 12 of the first segmentation file 10 is displayed in a solid line and the segmentation 12' of the second segmentation file 10' is displayed in a dotted line superimposed thereupon. In one embodiment, the line types can be selected by "scrolling" with a mouse wheel or similar device. The cross-sectional display 68 thus shows roughly the conformance between the segmentations 12 and 12' of the standard and target segmentations.

Figure 6:
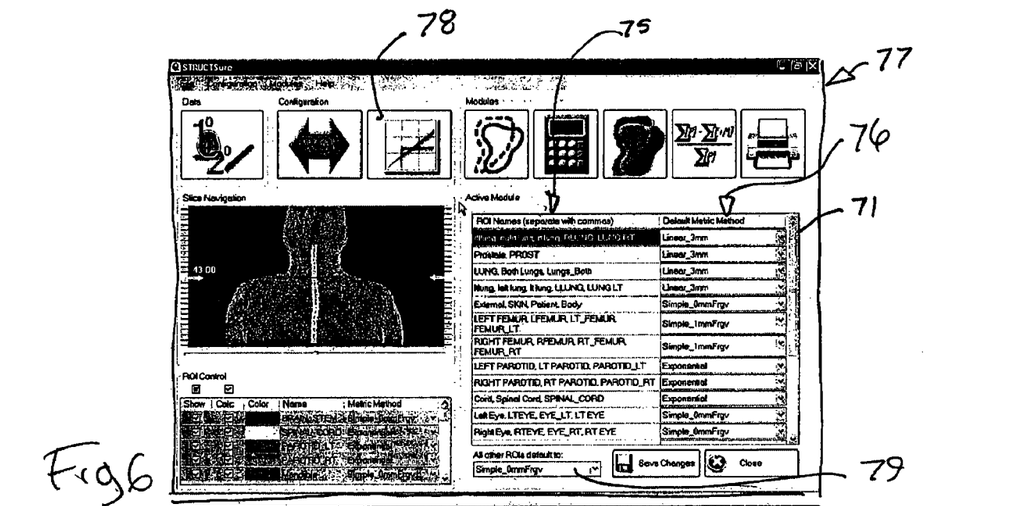
FIG. 6 is a figure similar to FIGS. 4 and 5 showing a table permitting the automatic matching of metric methods to particular structures by structure name in the electronic files.

Referring to FIGS. 3 and 6, at subsequent process block 69, a measurement metric for the comparison of the segmentations 12 and 12' is now identified. This identification of a measurement metric is performed using interface screen 77 invoked by pressing a measurement metric button 78.

The interface screen 77 displays an assignment of measurement metrics to particular structures 22 of the segmentations 12 and 12' in an assignment window 71 which links, in rows, one or more text names of structures in a first column 75 to titles of particular measurement metrics in a second row 76. Thus, for example, the structure 22 of the prostate represented by either of the text strings "Prostate" or "PROST" may be matched to a measurement metric entitled "linear_3 mm". This assignment window 71 represents an underlying table structure that may be initialized and modified by the user. The interface screen 77 provides a method of checking this assignment and of changing the particular measurement metric associated with a structure through drop-down menus listing other measurement metrics. Structures 22 that are not found in the table underlying assignment window 71 may use a default formula entered in text block 79.

Figure 7:
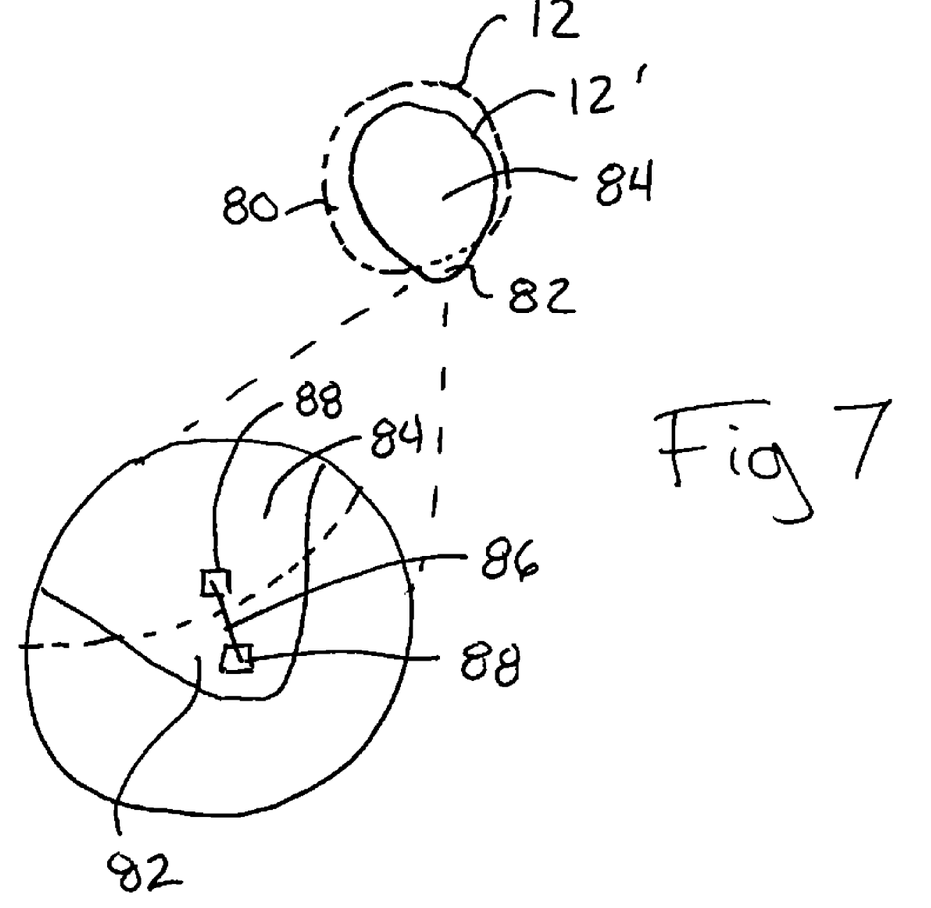
FIG. 7 is a simplified representation of two segmentation volumes in cross-section per the display of FIG. 5 showing different measurements made by the present invention.

A particular measurement metric may be preestablished formulas as will be described or may be defined by the user. Referring now to FIG. 7, in either case, the measurement metrics receive data indicating how well the compared segmentation 12' matches the standard segmentation 12 in terms of their volumetric overlap. Generally, the data for the measurement metric is prepared by first identifying "missing" volume elements 80 in the segmentation 12' that are not in the standard segmentation 12. Next, "extra" volume elements 82 that are found in the standard segmentation 12 but not in the compared segmentation 12 are identified. Finally, "common" volume elements 84 that are found in both the standard and the compared segmentations 12 and 12' are identified.

In addition, a scalar distance 86 between each given volume element 88 in either of the missing volume elements 80 or extra volume elements 82 (only the latter shown) and the closest volume element 88' in the common volume elements 84 is determined. Alternatively, this scalar distance 86 may be a center of gravity or similar measurement of the region of the missing volume elements 80 or extra volume elements 82.

Each measurement metric may provide a different treatment of one or more of these volume elements and scalar distances.

Figure 8:
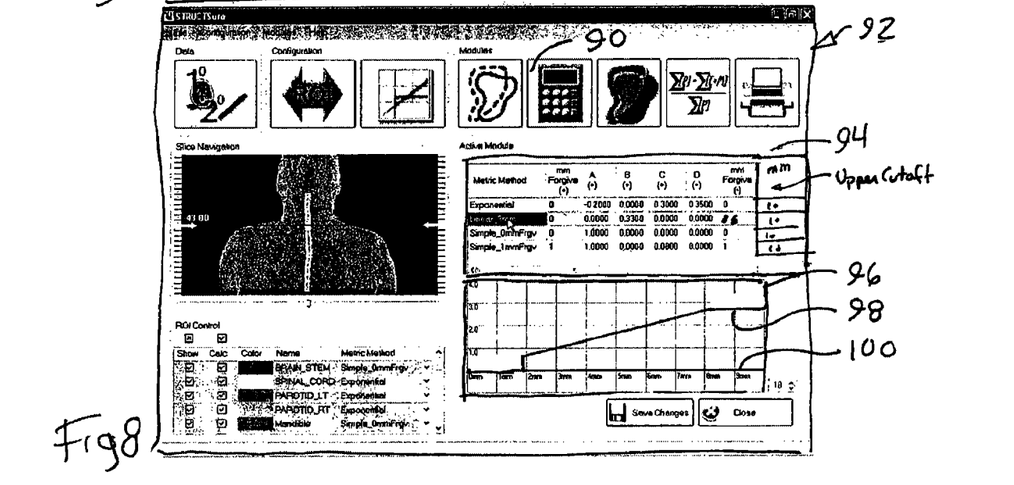
FIG. 8 is an interface screen used for defining a metric method such as is used in the table of FIG. 6.

Referring now to FIG. 8, clicking menu button 90 invokes an interface screen 92 that allows custom entry of metric methods through formula parameter table 94 and a formula graph 96. The formula parameter table 94 allows the user to develop their own formulas and to name them with a text string per the first column of the formula parameter table 94 entitled: "metric methods". This same title will be used in table of assignment window 71 of FIG. 6.

The row following the name of the metric method permits the user to enter a set of parameters for the desired metric method. The particular parameters include: "mm Forgive (+)", mm UpperCutoff(+), "A(+)", "B(+)", "C(+)", and "D(+)" being associated with extra volume elements 82 and parameters "mm Forgive (−)", mm UpperCutoff(−), "A(−)", "B(−)", "C(−)", and "D(−)" being associated with missing volume elements 80. Generally the "mm Forgive" parameters describe a scalar distance 86 equal to or below which volume elements 80 or 82 are not counted and mm UpperCutoff(+) represents a limit beyond which volume elements 80 or 82 incur no further penalty. This allows small errors in conformance of segmentation 12 and segmentation 12' to be disregarded and large errors to be discounted.

The parameters A-D provide for weightings for the counting of volume elements 80 and 82 as functions of the distance 86. Parameter A provides a constant weighting (independent of distance) equal to the value of A according to the formula of $$W1=A.$$

Parameter B provide a linear weighting as a function of distance (d) according to the formula:

$$W2=B*d.$$

Parameters C and D provide an exponential weighting of the volume elements as a function of distance according to the formula:

$$W3=Ce^{dD}.$$

The metric method produces an evaluation number E that is equal to:

$$E = 100*\left[\frac{PV - VP}{PV}\right]$$

where PV is the number of common voxels and VP is the voxel penalty computed as follows:

$$VP = \sum_m \text{Penalty}(v_m) + \sum_e \text{Penalty}(v_e)$$

where $v_m$ are missing voxels and $v_e$ are extra voxels and the Penalty function for these voxels is a function of the distance 86 of each voxel as follows:

$$\text{Penalty}(v_i) = \begin{bmatrix} d(v_i) < \text{Forgive} & 0 \\ \text{Forgive} \le d(v_i) \le & \\ \text{UpperCutoff} & A + (B*d(v_i)) + Ce^{d(v_i)*D} \\ d(v_i) > \text{UpperCutoff} & A + (B*\text{UpperCutoff}) + \\ & Ce^{\text{UpperCutoff}*D} \end{bmatrix}$$

where the values of A, B, C and D are A(+), B(+), C(+), and D(+) respectively for the extra volume elements 82 and A(−), B(−), C(−), and D(−) respectively for the missing volume elements 80. This parameterization allows for the fast generation of complex metric methods on a custom basis. Below the table 94, the graph 96 plots the metric method as plot line 98 for the extra volume elements 82 (the first summation in the above formula) and plot line 100 for the missing volume elements 80 (the second summation in the above formula).

Alternatively, the user may enter any mathematical formula combining the data described above relating to the scalar distance and number of missing, extra, and common voxels.

Referring again to FIG. 3, once the proper metric methods have been developed and associated with a particular structure 22, as indicated by process block 101, the electronic segmentation files 10 and 10' which describe segmentations 12 and 12' are "voxelized". This process takes the segmentations 12 and 12', which are constructed of a set of points 102 together forming closed curve for each of multiple cross-sectional planes, and creates a voxel model 104 conforming generally to the bounded volume. In the preferred embodiment, each voxel is cubic with 1 mm or smaller edge dimensions.

This process of converting these segmentations 12 and 12' to a voxel model may be conducted by a suitable technique for determining points inside of a complex and potentially bifurcated surface, the likes of which are known in the field of image processing and image generation. One method would be to discretize 3D space into an orthogonal voxel grid, then analyze each voxel to see if the center of the voxel lies inside the areas encompassed by the closed loop 2D ROI contours specified in the structure set, allowing multiple close loop areas for bifurcated ROIs (i.e. when more than one closed loop is assigned to a single ROI for one slice). Voxels that fall in between slices could be analyzed based on either: a) the 2D contours of the nearest slice, or b) interpolated 2D contours based on the surrounding planes.

Upon completion of this process of building voxel models, per process block 101 at process block 108, the voxel models are adjusted for any origin offsets previously entered by the user (per interface screen 52) so that the voxel models are aligned in a common reference space with respect to the structure 22 they define. Once this process is complete, then at process block 111, a comparison of the voxel models for the segmentations 12 and 12' is conducted characterizing each of the voxels 106 as common, missing, or extra as described above, and determining the scalar distances also described above as indicated by process block 140 of FIG. 3.

Figure 9:
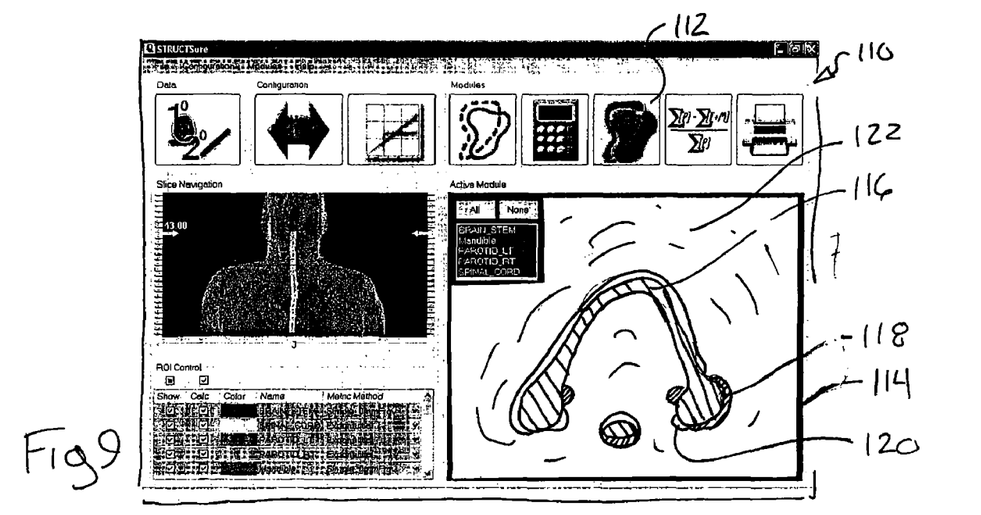
FIG. 9 is a display of a graphical representation of the conformance of the segmentations per a metric method.

Referring now to FIG. 9, a next interface screen 110 may be invoked by pressing the menu button 112, which provides an analysis window 114 for displaying the segmentations in a manner similar to that described with respect to FIG. 5 but shaded inside the outlines to separately indicate the volume elements that are common, missing, or extra. In the preferred embodiment, common volumes 116 are shaded green, the missing volumes 118 are shaded blue, and the extra volumes 120 are shaded red. The images of the shaded volumes may be superimposed over an image of the actual structure 122 as was acquired with respect to the interface screen 52 described in FIG. 4.

This evaluation of the common, missing, and extra volume elements may be performed simply by evaluating in turn each of the voxels in a set comprising the union of all voxels in the first and second voxel model to identify if they have a counterpart in the other model. Alternatively, it will be understood that this process can be conducted without a voxelization, for example, by approximating the volumes using a set of thin rectangular areas in each cross-sectional plane and computing the intersection of these areas using graphical algebraic techniques.

Figure 10:
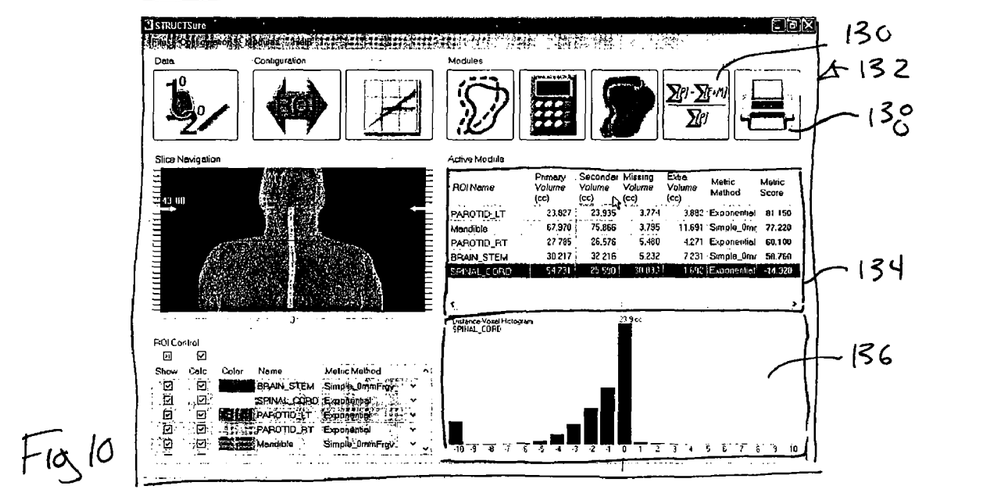
FIG. 10 is a quantitative display of the result of the comparison of the segmentations per a metric method.

Referring now to FIG. 10, pressing menu button 130 invokes an interface screen 132 providing for a quantitative evaluation of the comparison of the two segmentations 12 and 12'.

This evaluation may be performed simultaneously on multiple structures as output through a table 134 which may indicate the following quantitative values:

(1) primary volume (volume in cubic millimeters or centimeters of the standard segmentation 12);

(2) secondary volume (volume in cubic millimeters or centimeters of the compared segmentation 12);

(3) missing volume (volume in cubic millimeters or centimeters of the missing volume elements 80);

(4) extra volume (volume in cubic millimeters or centimeters of the extra volume elements 82); and (5) metric method/metric score (the name of the metric method and the resulting evaluation.)

A histogram table 136 tallies the voxels of the missing and extra volumes according to a distance measurement bin. In this example, the voxels of the missing volume elements are plotted extending to the left of the zero point and the voxels of the extra volume elements are plotted to the right of the zero point.

A report may be printed by pressing menu button 138.

The present invention may be used in the training of clinicians on general contouring (critical structures and target delineation) by comparing their contouring to user-defined standards or for periodic quality assurance testing of anatomy auto-segmentation routines and systems by comparing auto-segmented volumes to user defined standards. In addition the present invention may be used to make assessments of anatomy auto-segmentation routines or systems prior to customer purchase or clinical application or for the assessment of auto-segmentation routines or systems against updated and new imaging technology.

The output of the system (e.g., the segmentation of valuations) as indicated by process block 140 of FIG. 3, may also be used to assess whether a new treatment plan should be prepared based on changes in the internal anatomy of the patient during radiation therapy reflected in the new segmentation.

It is specifically intended that the present invention not be limited to the embodiments and illustrations contained herein, but include modified forms of those embodiments including portions of the embodiments and combinations of elements of different embodiments as come within the scope of the following claims

We claim:

1. An apparatus for automatically assessing radiation therapy segmentations comprising an electronic computer executing a stored program to:
   (a) receive a first and second electronic file each providing data points describing different three-dimensional surfaces circumscribing a structure in a human or animal patient intended for radiation therapy;
   (b) generate a first and second volume model defined by the different three-dimensional surfaces of the first and second electronic file respectively;
   (c) compare the first and second volume model to identify:
      (i) common volume elements in common to both of the first and second volume models;
      (ii) missing volume elements of the first volume model that are not in the second volume model; and
      (iii) extra volume elements of the second volume model that are not in the first volume model; and
   (d) output an indication of a conformance between the three-dimensional surfaces circumscribing the structure defined by the first and second electronic files based on a metric method of measuring volumes of the missing volume elements and extra volume elements;
   whereby segmentation represented by the second electronic file is evaluated.

2. The apparatus of claim 1 wherein the first and second volume models are constructed by identifying a set of voxels within the three-dimensional surfaces, and wherein the step of comparing the first and second volume models evaluates each voxel of a union of the set of voxels of the three-dimensional surfaces on a voxel by voxel basis to measure the missing and extra volume elements.

3. The apparatus of claim 1 wherein the electronic computer further includes a graphic display screen and wherein the stored program further displays a cross-sectional image through the first and second volume models along a user-defined cross-sectional plane separately identifying the common volume elements, missing volume elements, and extra volume elements by different colors.

4. The apparatus of claim 3 wherein the common volume elements are colored green, the missing volume elements colored blue and the extra volume elements colored red.

5. The apparatus of claim 3 wherein the stored program further receives a third electronic file providing a cross-sectional image of patient tissue at the user defined cross-sectional plane, and wherein cross-sectional images through the first and second volume models are displayed superimposed on the cross-sectional image of patient tissue obtained from a third electronic file.

6. The apparatus of claim 1 wherein the metric method provides a weighted sum of missing volume elements and extra volume elements normalized by a number of common volume elements so that the metric score decreases with increasing missing volume elements and extra volume elements.

7. The apparatus of claim 1 wherein the step of comparing the first and second volume models also identifies a distance measure for each missing volume element from a closest common volume element and a distance measure for each extra volume element from a closest common volume element wherein the distance measure provides a weighting of the volume of the missing volume elements and extra volume elements in the metric method.

8. The apparatus of claim 1 wherein the electronic computer further includes a user input device for accepting a representation of the metric method to allow a user to set the metric method.

9. The apparatus of claim 8 wherein the metric method is a combination of:
(i) a constant value,
(ii) a linear function of a number of error volume elements with distance, and
(iii) an exponential function of the number of error volume elements with distance;
wherein the error volume elements are missing volume elements or extra volume elements.

10. The apparatus of claim 1 wherein the electronic computer further includes a graphic display screen and wherein execution of the stored program produces a histogram displaying cumulative missing volume elements as a function of distance ranges and cumulative extra volume elements as the function of distance ranges.

11. The apparatus of claim 1 wherein the first and second electronic files provide text strings identifying the structure and wherein the stored program provides for a selection of the metric methods used for the measurement from a set of metric methods using a table mapping the text strings identifying the structure of the first and second electronic files to one of the set of metric methods to be used as the metric method.

12. The apparatus of claim 1 wherein the electronic computer further includes a graphic display screen and a user input device for accepting function parameters; and
wherein the stored program executes to display a function of the metric method as a graph together with function parameters entered by the user and to change the graph as the function parameters are changed by the user.

13. A method for automatically assessing radiation therapy segmentations comprising using an electronic computer executing stored program to perform the steps of:
(a) receiving a first and second electronic file each providing data points describing different three-dimensional surfaces circumscribing a structure in a human or animal patient intended for radiation therapy;
(b) generating a first and second volume model defined by the different three-dimensional surfaces of the first and second electronic file respectively;
(c) comparing the first and second volume model to identify:
(i) common volume elements in common to both of the first and second volume models;
(ii) missing volume elements of the first volume model that are not in the second volume model; and
(iii) extra volume elements of the second volume model that are not in the first volume model; and
(d) outputting an indication of a conformance between the three-dimensional surfaces circumscribing the structure defined by the first and second electronic files based on a metric method of measuring volumes of the missing volume elements and extra volume elements;
whereby segmentation represented by the second electronic file is evaluated.

14. The method of claim 13 wherein the first and second volume model are constructed by identifying a set of voxels within the three-dimensional surfaces, and wherein the step of comparing the first and second volume models evaluates each voxel of a union of the set of voxels of the three-dimensional surfaces on a voxel by voxel basis to identify the missing and extra volume elements.

15. The method of claim 14 further including the step of displaying a cross-sectional image through the first and second volume models along a user-defined cross-sectional plane separately identifying the common volume elements, missing volume elements, and extra volume elements by different colors.

16. The method of claim 13 wherein the common volume elements are displayed as green, the missing volume elements are displayed as blue and the extra volume elements are displayed as red.

17. The method of claim 16 wherein the common volume elements, missing volume elements and extra volume elements are displayed superimposed on the cross-sectional image of patient tissue showing the structure.

18. The method of claim 14 wherein the step of comparing the first and second volume models also identifies a distance of each missing volume element from a closest common volume element and a distance of each extra volume element from a closest common volume element and wherein the measure is based on a metric method of the missing volume elements and extra volume elements weighted by the respective distances.

* * * * *